US009393159B2

(12) United States Patent
Nokes, Jr.

(10) Patent No.: US 9,393,159 B2
(45) Date of Patent: Jul. 19, 2016

(54) SELF-ADHERING CARRIER FOR AN ADHESIVE BANDAGE

(71) Applicant: Redpoint International Inc., Vancouver, WA (US)

(72) Inventor: Charles E. Nokes, Jr., Vancouver, WA (US)

(73) Assignee: REDpoint International Inc., Vancouver, WA (US)

( * ) Notice: Subject to any disclaimer, the term of this patent is extended or adjusted under 35 U.S.C. 154(b) by 686 days.

(21) Appl. No.: 13/671,465

(22) Filed: Nov. 7, 2012

(65) Prior Publication Data

US 2014/0128790 A1     May 8, 2014

(51) Int. Cl.
*A61F 13/02*     (2006.01)
*A61F 15/00*     (2006.01)
*A61F 13/00*     (2006.01)

(52) U.S. Cl.
CPC ....... *A61F 13/0259* (2013.01); *A61F 13/00085* (2013.01); *A61F 15/006* (2013.01); *A61F 13/0269* (2013.01); *A61F 13/0273* (2013.01); *A61F 2013/00553* (2013.01)

(58) Field of Classification Search
CPC .............. A61F 13/00; A61F 13/00004; A61F 13/00021; A61F 13/00029; A61F 13/02; A61F 13/0269; A61F 13/0273; A61F 2013/00089; A61F 2013/00217; A61F 2013/00553; A61F 2013/00565; A61F 2013/00655; A61F 2013/00723; A61F 15/00; A61F 15/006; A61F 2013/00557; A61F 2013/00561
USPC ............ 602/41, 42, 53, 54, 58, 60, 75, 78, 79
See application file for complete search history.

(56) References Cited

U.S. PATENT DOCUMENTS

| 4,909,243 | A | * | 3/1990 | Frank et al. | ....................... 602/58 |
| 5,456,660 | A | * | 10/1995 | Reich et al. | ....................... 602/79 |
| 7,160,262 | B2 | * | 1/2007 | Wicks | .............................. 602/19 |

* cited by examiner

*Primary Examiner* — Keri J Nelson
(74) *Attorney, Agent, or Firm* — Chernoff, Vilhauer, McClung & Stenzel, LLP

(57) ABSTRACT

A self-adhering carrier enables application of an adhesive bandage without contact between the bandage's adhesive and the skin.

4 Claims, 2 Drawing Sheets

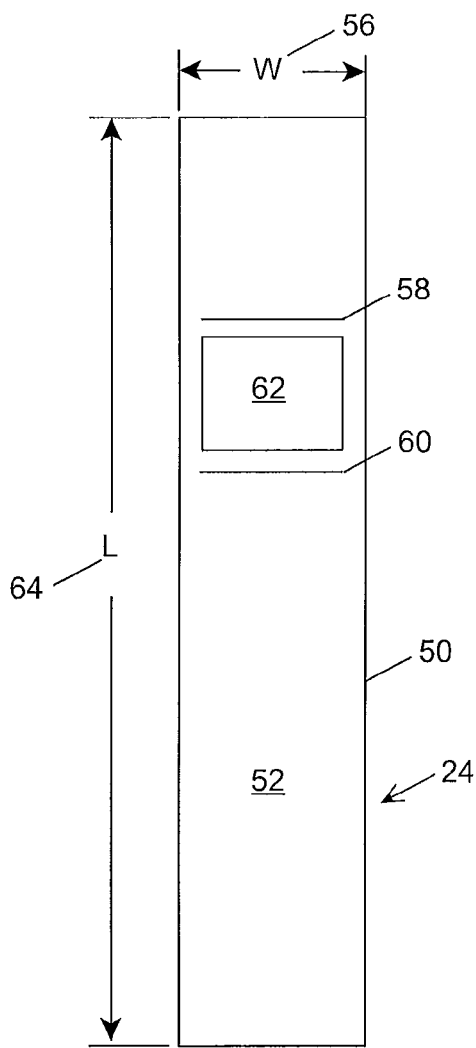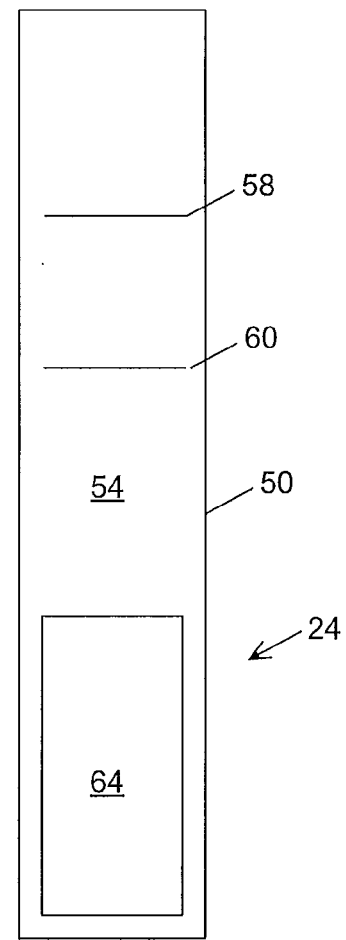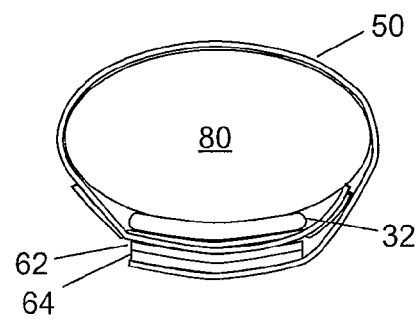
FIG. 4    FIG. 5
FIG. 6

SELF-ADHERING CARRIER FOR AN ADHESIVE BANDAGE

CROSS-REFERENCE TO RELATED APPLICATIONS

Not applicable.

BACKGROUND OF THE INVENTION

The present invention relates to a bandage for covering a wound and, more particularly, to a self-adhering carrier for an adhesive bandage.

Adhesive bandages are easy to use, relatively inexpensive and available in a variety of types, shapes and sizes. Adhesive bandages are widely used in hospitals, workplaces and homes to protect minor wounds from contamination and further injury and to maintain contact between a medicant and a wound. Adhesive bandages typically comprise a backing, an absorbent wound contact portion and a pressure sensitive adhesive coating that is applied to one or more areas on a face of the backing. The pressure sensitive adhesive enhances the utility of the bandage by enabling adherence of the bandage to itself and to the user's skin and making self-application of the bandage more feasible.

The wound contact portion of an adhesive bandage commonly comprises an absorbent pad or cushion which is adhered to the backing. The pad or cushion absorbs bodily exudates from the wound and prevents contact between the adhesive and the wound which might reinjure the wound when the bandage is removed. However, the cushion or pad reduces the flexibility of a bandage and limits its usefulness particularly when used on an area of the body which is subject to frequent or exaggerated movement. Padless adhesive bandages having wound contact portions comprising a hydrocolloid to absorb exudates and reduce the strength of the adhesive bond to protect the wound are particularly useful for application to high movement areas of the body.

The pressure sensitive adhesive should provide sufficient adhesion and flexibility to retain the bandage on the skin but not so much adhesion that the skin is damaged when the bandage is removed. However, in some cases it necessary to change a bandage frequently to medicate the wound or check on the progress of healing and frequent removal of an adhesive bandage can cause trauma to the skin even if the skin is relatively healthy. In addition, the skin of patients with poor circulation, for examples, older persons or persons with diabetes, can be more easily damaged during bandage removal and the damage may pose serious risks. Moreover, it is known that a significant portion of the population is allergic to the adhesives used in adhesive bandages. Adhesive to skin contact, particularly for prolonged periods of time, may cause a skin rash in up to 50% of the population. Usually the skin rash is minor and will disappear without treatment in a few days following removal of the adhesive from the skin. However, a substantial portion of the population may experience a severe allergic reaction, such as allergic contact dermatitis, requiring treatment and reappearing if the adhesive allergen is applied to a previously affected area at a later time.

What is desired, therefore, is a low cost bandage having the convenience an adhesive bandage but which does not expose the user's skin to bandage adhesive.

BRIEF DESCRIPTION OF THE DRAWINGS

FIG. 4 is a plan view of a first face of a carrier for an adhesive bandage.

FIG. 5 is a plan view of an opposing second face of the adhesive bandage carrier of FIG. 4.

FIG. 6 is an elevation view of a self-adhering bandage installed on an appendage.

DETAILED DESCRIPTION OF PREFERRED EMBODIMENTS

Figure 1:
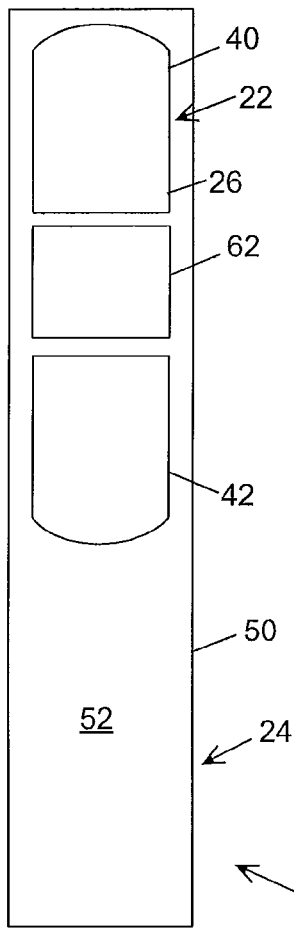
FIG. 1 is a plan view of one face of a self-adhering bandage comprising an adhesive bandage and a self-adhering carrier.
Figure 2:
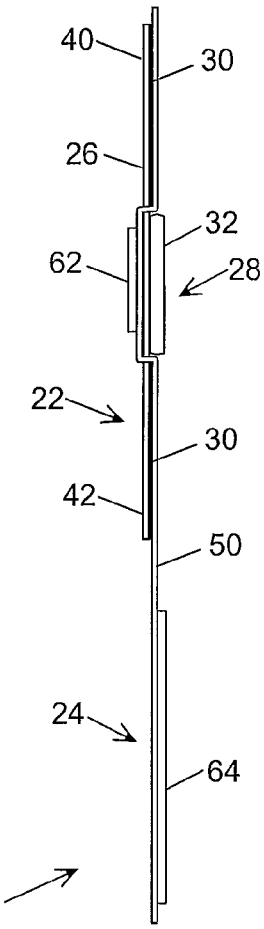
FIG. 2 is an elevation view of the self-adhering bandage of FIG. 1.
Figure 3:
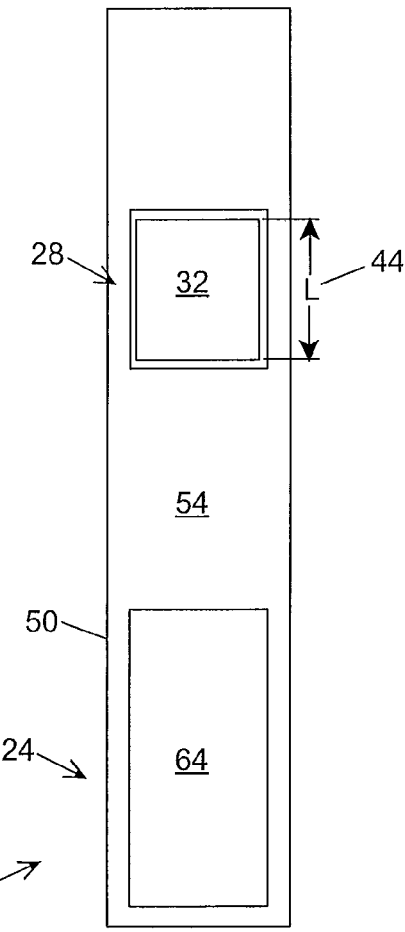
FIG. 3 is a plan view of an opposing second face of the self-adhering bandage of FIG. 1.

Adhesive bandages are widely used to protect minor wounds from contamination and promote healing. Adhesive bandages are relatively inexpensive; available in a wide range of sizes, materials and shapes and convenient to use enabling a user to apply the bandage to his/herself without assistance. However, a significant portion of the population is known to suffer skin damage when an adhesive bandage is removed or experience an allergic reaction to the adhesive used with adhesive bandages. The inventor concluded that a self-adhering carrier for an adhesive bandage which precludes adhesive to skin contact would avoid problems resulting from adhesive contact with the skin while retaining the economy and convenience of an adhesive bandage. Referring in detail to the drawings where similar parts are identified by like reference numerals, and, more particularly to FIGS. 1-3, a self-adhering bandage 20 comprises, generally, an adhesive bandage 22 and a self-adhering carrier 24. An adhesive bandage typically comprises a fabric or plastic backing 26, a wound contact portion 28 exposed on a face of the backing and a pressure sensitive adhesive 30 that is applied to one or more areas of a face of the backing, typically, the same face of the backing on which the wound contact portion is exposed. The wound contact portion 28 of the exemplary adhesive bandage 22 comprises an absorbent pad 32 or cushion that is adhered to the face of the backing 26. The pad protects the wound from contact, absorbs exudates from the wound and prevents adhesion of the backing to the wound which could cause injury to the wound when the bandage is removed. However, a pad reduces the flexibility of an adhesive bandage and padless adhesive bandages are available and particularly useful for bandaging areas of the body where movement is frequent or extensive. The wound contact portion 28 of a padless bandage typically comprises an area of the backing to which a hydrocolloid is applied. The hydrocolloid absorbs moisture and may be combined with other materials to reduce the bond strength of the adhesive to protect the wound.

Referring also to FIGS. 4 and 5, the self-adhering carrier 24 for the adhesive bandage 22 comprises a body portion 50 of flexible, preferably gas porous, sheet material, for example, a polypropylene fabric or a paper based material, that is adhesive free or does not expose the skin to contact with an adhesive but which may adhere to itself. Generally, the body portion 50 has a first face 52 and an opposing second face 54 and a shape similar to the adhesive bandage with which is it will be used. For example, for use with the exemplary elongate, adhesive bandage 22, the body 50 of the carrier 24 is an elongate rectangle. The width 56 of the carrier's body 50 is slightly greater than the width of the adhesive bandage 22 with which it will be used. The body 50 includes portions defining spaced apart, plural transverse slits 58, 60. The transverse slits 58, 60 of the carrier are preferably centered laterally in the carrier's body 50 and are of sufficient width to enable passage of end portions 40, 42 of the backing 26 of the adhesive bandage 22. The slits 58, 60 are spaced apart approximately the length 44 of the contact portion 28 of the adhesive bandage 22 so that when the end portions 40, 42 of the adhesive bandage are passed through the slits 58, 60 and adhered to the outer face 52 of the carrier, the contact portion 28 of the adhesive bandage will be exposed for engagement with the user's skin on the second face 54 of the carrier. However, the wearer's skin, including the wound area, will be protected from exposure the adhesive 30 which is applied to the end portions 40, 42 of the adhesive bandage's backing 26 and adhered to the opposing outer face 52 of the carrier's body 50. By adhering the end portions 40, 42 of the adhesive bandage 22 to the outer face 52 of the carrier 24, the body 50 of the carrier imposes a barrier between the adhesive and the wearer's skin.

The body 50 of the carrier 24 may comprise a material, such as a self-adhering gauze, which adheres to itself but does not expose a user to an adhesive or adhere the user's skin or may include a fastening system securable to prevent relative movement of the opposing faces of the carrier. The exemplary carrier 24 comprises a non-adhesive material to which are attached elements 62, 64 of a hook and loop fastening system. One element 62, preferably the hook element, is secured to the first face 52 of the carrier's body 50, preferably between the plural slits 58, 60 and opposite the intended position on the second face of the carrier of the exposed contact portion 28 of the installed adhesive bandage 22. The second element 64, preferably the loop element, is attached to the second face 54 of the carrier's body proximate the end of the body distal of the location of the hook portion. The hook and loop fastener elements 62, 64 can be attached to the carrier by sewing, radio-frequency (RF) welding or any other method compatible with the materials of the hook and loop elements and the carrier's body and suitable for contact with the wearer's skin. Referring also to FIG. 6, the length 64 of the carrier 24 should be sufficient to enable the carrier to be wrapped around a wounded portion of the body, for example, the appendage 80, and to allow a first portion of the carrier's body to adhere to a second portion or to allow one element of the fastening system, for example, element 62, to engage the second element 64 of the fastening system. Carriers can be produced in widths and lengths convenient for use with particular ones of the wide ranges of sizes of adhesive bandages, but an end portion of a longer carrier, for example, a carrier of sufficient length to encircle the torso, may be cut so that the length is appropriate for use with a specific wounded portion of the body. By locating the element 62 of the exemplary fastening system in opposition to the wound contact portion 28 of the adhesive bandage 22 tension in the body 50 of the carrier produces pressure on the wound contact portion keeping the wound contact portion securely in contact with the wound.

The self-adhering carrier for an adhesive bandage protects the wearer's skin from harmful contact with bandage adhesive while retaining the convenience and low cost of an adhesive bandage.

The detailed description, above, sets forth numerous specific details to provide a thorough understanding of the present invention. However, those skilled in the art will appreciate that the present invention may be practiced without these specific details. In other instances, well known methods, procedures, components, and circuitry have not been described in detail to avoid obscuring the present invention.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

I claim:

1. A self-adhering bandage comprising:
   (a) an adhesive bandage including a wound contact portion, an adhesive and a backing, said adhesive and said wound contact portion exposed on a first face of said backing; and
   (b) an elongate flexible carrier having a first face and an opposing second face and including portions defining a first transverse slit arranged to receive a first end portion of said backing and a second transverse slit arranged to receive a second end portion of said backing, said first slit spaced apart from said second slit to expose said wound contact portion on said second face of said carrier when said first and second end portions of said backing are received in said first slit and said second slit and adhered to said first face of said carrier.

2. The self-adhering bandage of claim 1 further comprising a fastening system including:
   (a) a first fastening element secured on said first face of said carrier; and
   (b) a second fastening element securable to said first fastening element and secured on said second face of said carrier.

3. The self-adhering bandage of claim 1 further comprising:
   (a) a hook element of a hook and loop fastening system attached to one of said first face of said carrier and said second face of said carrier; and
   (b) a loop element of said hook and loop fastening system attached to the other of said first face of said carrier and said second face of said carrier, said hook element engageable with said loop element to secure of portions of said carrier against relative movement.

4. The self-adhering bandage of claim 3 wherein one of said hook element and said loop element is secured on said first face of said carrier at a location opposite of a location on said second face of said carrier where wound contact portion of said adhesive bandage is exposed.

* * * * *